(12) United States Patent
Schmitz et al.

(10) Patent No.: US 7,725,163 B2
(45) Date of Patent: May 25, 2010

(54) SYSTEM AND METHOD WITH AUTOMATICALLY OPTIMIZED IMAGING

(75) Inventors: Georg Schmitz, Wachtberg (DE); Henning Braess, Aachen (DE); Harald Reiter, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 870 days.

(21) Appl. No.: 10/324,416

(22) Filed: Dec. 19, 2002

(65) Prior Publication Data

US 2003/0120145 A1 Jun. 26, 2003

(30) Foreign Application Priority Data

Dec. 21, 2001 (DE) ................................ 101 63 215

(51) Int. Cl.
*A61B 6/00* (2006.01)
(52) U.S. Cl. .................. 600/425; 600/407; 600/427; 600/428; 600/429; 600/437; 378/8; 378/65; 378/69; 378/95
(58) Field of Classification Search ................ 600/425, 600/407, 427, 429, 437, 439; 378/8, 65, 378/69, 95
See application file for complete search history.

(56) References Cited

U.S. PATENT DOCUMENTS 3,839,634 A * 10/1974 Buchmann ............ 250/214 VT
5,513,239 A * 4/1996 Mulder ...................... 378/98.7
5,873,830 A * 2/1999 Hossack et al. ............. 600/447
6,047,043 A * 4/2000 Kamps ...................... 378/98.7
6,139,183 A * 10/2000 Graumann .................. 378/206
6,295,336 B1 * 9/2001 Aach et al. .................. 378/108
6,295,464 B1 * 9/2001 Metaxas ..................... 600/407
6,385,474 B1 * 5/2002 Rather et al. ................ 600/407
6,501,981 B1 * 12/2002 Schweikard et al. ........ 600/427
6,524,246 B1 * 2/2003 Kelly et al. ................. 600/437
6,690,965 B1 * 2/2004 Riaziat et al. ............... 600/428
6,778,689 B1 * 8/2004 Aksit et al. ................. 382/128
6,795,524 B2 * 9/2004 Hayashi .................... 378/98.12
6,937,696 B1 * 8/2005 Mostafavi ................... 378/95

FOREIGN PATENT DOCUMENTS

EP          0 435 528          7/1991
EP          0 748 148          12/1996

OTHER PUBLICATIONS

Public Disclosure 4-2332, Jan. 7, 1992; Patent application 2-106100, Apr. 20, 1990; Application Toshiba Co., Ltd.

* cited by examiner

*Primary Examiner*—Brian Casler
*Assistant Examiner*—Baisakhi Roy

(57) ABSTRACT

An image system, notably an X-ray system and an ultrasound system, is provided in which images or sequences of images are generated and used to automatically change or optimize the operational behavior of individual image system components. Measurement fields are defined in the images of an image sequence by means of a data processing unit. Information is extracted from the measurement fields in order to adapt the system components. More specifically, in the course of a sequence of images the measurement fields are adapted or shifted in conformity with the motion of objects.

11 Claims, 2 Drawing Sheets

SYSTEM AND METHOD WITH AUTOMATICALLY OPTIMIZED IMAGING

BACKGROUND

The invention relates to an X-ray system and an ultrasound system which generate images or sequences of images and modify or optimize the operational behavior of individual system components. The invention also relates to a method of controlling such system components.

During a medical X-ray examination by means of a series of X-ray images, the physician is often confronted with the problem of having to adjust, in addition to carrying out the actual examination, also the operational behavior of individual components of the X-ray examination system in order to achieve an optimum quality of the X-ray images in the image regions of interest. Optimum adjustment of the X-rays is of particular importance. On the one hand, an increase of the radiation dose usually enhances the image quality, but on the other hand the object to be examined should be exposed to an as small as possible radiation dose only. The requirements imposed on the image quality as a result thereof are normally defined by the type of examination while minimizing at the same time the radiation dose for the object to be examined. Various possibilities are known for automatic control of the X-ray dose by the system. To this end, during operation the system usually extracts information from images or image regions in order to readjust the dose automatically on the basis thereof. When the X-ray dose is controlled on the basis of the complete image contents, such control often leads to unsatisfactory results because the control is adversely affected by changing image regions and image regions which are strongly overexposed or underexposed because of properties that are inherent of the system. Therefore, for example, the documents EP 0435528 and EP 0748148 disclose X-ray systems which extract information for dose control from predetermined image regions, that is, so-called regions of interest or ROI, instead of from the entire image.

These systems, however, have the drawback that the ROI is predetermined and hence static. This gives rise to the problem that the object region to be examined must be imaged in the image region of the ROI. If this is not the case, the dose will be controlled on the basis of incorrect image data. When a moving object is examined by means of series of images, the object is liable to leave the static ROI because of its motion, so that the dose control again operates on to basis of incorrect image data. In order to mitigate this problem, for example, the object or the system could be positioned anew, usually implying an unacceptable amount of additional work for the staff, or the ROI could be enlarged, be it at the expense of a degradation of control. For the adjustment of different system parameters it is necessary to use information from different ROIs.

The document JP 04002332 discloses an X-ray examination system for use during heart catheterizations; this system supports the physician in positioning a catheter on the basis of a rectangular image section which is taken from a larger image and which shows the tip of the catheter at the center and automatically follows the catheter during its motion. The selection and shifting of the rectangular section are carried out by means of a simple motion analysis in which two successive images are subtracted. Further aids, notably means for simplifying the operability of the system, are not made available to the physician. This system has the drawback that the images wherefrom the image section is taken must always be larger than the image section which contains the information of interest to the physician. Consequently, an unnecessarily large region of the patient is exposed to X-rays. Moreover, the image quality is not changed.

SUMMARY

It is an object of the invention to provide an imaging system with automatic adaptation of the image quality, notably in image regions of interest, as well as to provide a corresponding method.

This object is achieved in accordance with the invention by means of a first embodiment of an X-ray system for generating X-ray images which includes a data processing unit which is arranged to form at least one measurement field from a plurality of image points of an X-ray image, and to control the X-rays by means of information extracted from the measurement field.

An X-ray system in accordance with the invention includes an X-ray source and an X-ray detector in addition to the data processing unit. An object to be examined, or a region of an object to be examined, is usually situated between the X-ray source and the X-ray detector. In the activated state of the X-ray source the X-rays penetrate the object and an X-ray image is formed on the X-ray detector in known manner, said X-ray image being converted into an electronic version. This electronic image is applied to the data processing unit in which it is further processed as well as to further system components, such as storage media or visualization means, which are not further specified herein. When single images are generated in fast temporal succession, an X-ray image sequence is formed which represents, for example, an object in motion as in a film.

Generally speaking, an X-ray image can be subdivided into regions which are of more interest and regions which are of less interest to the viewer. Such regions of interest should be imaged as well as possible; this can be achieved by suitable adaptation of the X-rays in relation to the regions of interest. The X-rays can be adjusted in various known manners by utilizing a variety of means which are dependent on the configuration of the system. For example, the characteristic of the X-rays can be adjusted by variation of the operating voltage of the X-ray tube. Variation of the X-ray current enables adjustment of the amount of radiation emitted per unit of time. Furthermore, the radiation emitted by the X-ray tube can be influenced by diaphragms, thus enabling location-dependent attenuation of the X-rays.

In the X-ray system in accordance with the invention the adaptation of the X-rays is achieved in that the data processing unit forms at least one measurement field from an image. A measurement field represents a number of image points which is dependent on the image contents, said image points being particularly suitable for the extraction of information in respect of the image quality. Conclusions as regards the quality of the image region covered by the measurement field can be drawn on the basis of this information, thus enabling adaptation of the X-rays to the required quality without utilizing information from non-relevant image regions. One item of information extracted from a measurement field in order to adjust the X-rays may be, for example, the mean value of the value of all image points in the measurement field. When this mean value exceeds a given limit value, the exposure in the region of the measurement field is too high and must be reduced. Another item of information is, for example, the grey value distribution (histogram) of the image points in the measurement field. If the grey value distribution is not homogeneously enough or too one-sided, the contrast of the image must be increased; this is possible, for example, by way of a modified characteristic of the X-rays. A further item of information may be the previously mentioned noise component of the image. If this component is known, for example, the radiation dose can be increased so as to reduce the noise.

An image point is associated with a measurement field, for example, when its value has changed in a statistically relevant manner in comparison with at least one previous image, that is, when the statistical comparison of its value with a value from at least one previous image yields a positive result. Such a statistical comparison provides a conclusion as regards the change of the value of an image point in a sequence of images. Generally speaking, such a comparison can be performed for each image point of an image. It has been found that the image points associated with a measurement field need not directly neighbor one another and that the edge of a measurement field may assume arbitrary geometrical shapes. For example, when the change of an image point exceeds a selectable value, it can be assumed with a high degree of probability that the change is not caused by noise; the image point thus constitutes a part of a moving object and is associated with the measurement field. In this example the statistical comparison may be considered as a motion detection operation. A further comparison in respect of the statistical relevance may consist, for example, in the examination of the part of the noise which determines the accuracy of detail rendition in relation to the actual image signal in the overall image. In order to determine this signal-to-noise ratio in dependence on the intensity, as homogeneous as possible image regions, covered by one or more measurement fields, are statistically evaluated, thus enabling the extraction of a characteristic determining the static quantum noise. Because of physical conditions, the higher the noise, the larger the geometrical dimensions of the smallest reproducible object detail will be. The signal-to-noise ratio can be enhanced, for example, by increasing the dose.

A special type of X-ray system is conceived for the display of moving objects. For a medical X-ray examination system the human heart or the blood flow in a blood vessel may be stated as examples of moving objects. A system of this kind aims to form an optimum image of the image regions of interest despite the object motion. To this end, for example, a measurement field covering the moving object is formed in each image of a sequence of images. The measurement field is thus adapted to the object motion in the course of the image sequence. The measurement field is thus defined in an adaptive manner. Because the moving object is always covered by the measurement field, the information extracted from such measurement fields enables optimum adjustment of the system parameters. Because the moving object cannot leave the measurement field under the influence of its motion, as in the case of static measurement fields, changing of the X-rays on the basis of irrelevant image information is avoided. If it is not necessary to adapt the shape and the magnitude of the measurement field in each image, for example, because of only a slight natural motion of the object, a further possibility for covering moving objects by means of a measurement field consists in defining first a measurement field which covers the moving object in an image by means of the above methods and in shifting this measurement field merely relative to the image in conformity with the directions of motion of the object, each time determined anew, in subsequent images. Such shifting requires less calculation capacity in the data processing unit. A further possibility of forming a measurement field is linked to the above considerations in respect of noise reduction: when the images of an image sequence show one or more moving objects, renewed definition of the measurement field in each image, for example, on the background, causes such a measurement field to be adapted to the shape of the background which changes in the course of the image sequence.

For the image quality of the image regions of interest it is of special importance that the radiation quality of the X-rays is adjusted so as to be as optimum as possible. In this context control of the dose (as a parameter of the radiation quality) can be particularly simply and efficiently realized, for example, by variation of the X-ray voltage, the current or the exposure duration by means of an X-ray system as disclosed in the originally claimed invention. Special advantages are also obtained for the imaging of moving objects, because more accurate and more exact control of the dose can be achieved in comparison with the state of the art.

A comparison in respect of the statistical relevance may advantageously consist of a motion detection operation in conformity with originally disclosed claims in which, for example, the variation in time of an image point is determined for a plurality of images. The image points which originate from a moving object are then associated with a measurement field, so that the image quality is adapted to the moving object to be imaged. In contrast therewith, in order to determine the noise component in the image a measurement field is formed from image points which can be associated with an as homogeneous as possible image region such as an image background. In addition the signal component in such an image region should vary only little in the course of the image sequence. When such a measurement field has been defined, the noise in an image can be determined on the basis of known relations between the image points of the measurement field.

In order to enable more reliable formation of a measurement field, further image points are associated with a measurement field in conformity with a further disclosed embodiment. Such further image points are image points which have a fixed spatial relationship with the image points already associated with the measurement field. For example, if only few image points are associated with a measurement field by means of the method as disclosed, for example, in order to avoid incorrect association in cases where it is difficult to estimate the motion because of a very noisy image, the measurement field becomes strongly fragmented. If further image points, for example, all direct neighbors of the already associated image points, are additionally associated with the measurement field, the fragmentation of the measurement field is reduced. In a further preferred embodiment, the geometrical relationship is defined in such a manner that all image points whose geometrical distance is less than a predetermined value are associated with the measurement field. If the distance is independent of direction, all image points which are situated within a circular area around already associated image points satisfy this criterion. The fragmentation of a measurement field is reduced when the majority of such circular areas overlap or contact one another. However, if it is found for an image point associated with the measurement field that the number of image points which are situated within the circular area and are not associated with the measurement field drops below a given value, the association is very likely incorrect and the image point is removed from the measurement field again.

A frequently examined organ is the human heart which performs complex and fast motions, leading to only inadequate automatic adjustment of system parameters in conventional systems. The use of an X-ray system in accordance with the invention for cardiological examinations, therefore, is particularly attractive. For example, the moving heart or parts thereof are then covered by at least one measurement field. During an examination the measurement field is adapted to the natural motions of the heart as well as to the relative motions towards the image edge and is displaced accordingly. This will be elucidated in detail, by way of example, in the description of the Figures given hereinafter. When the heart is examined by means of a catheter, the user should be able to track the tip of the catheter during given phases of the examination. For optimum imaging of the usually moving catheter, therefore, a measurement field which covers the catheter tip is defined in another disclosed embodiment.

An X-ray system in accordance with the invention is not only suitable for the control of X-rays. When the system includes further components which are controllable or whose operational behavior can be adapted, such control or adaptation can be performed by means of information extracted from measurement fields, that is, like for the control of the X-rays. Some examples in this respect will be given hereinafter. When it is determined on the basis of a measurement field that the image region of interest to the viewer tends to move out of the image due to motion, the X-ray system can be displaced relative to the object or the object or a table on which the object is arranged can be displaced relative to the X-ray system. The operational behavior of the X-ray detector can be modified by way of a plurality of parameters; in this respect, for example, the sensitivity, the image section or data compression can be adjusted. The image data can be processed by way of image processing algorithms in the data processing unit, the effect of an algorithm being adjustable by parameters. A visualization component such as a monitor can be adjusted, for example, in respect of image brightness or image contrast.

The object is also achieved by means of an ultrasound system for generating ultrasound images in conformity with another disclosed embodiment, which system includes a data processing unit which is arranged to form at least one measurement field from a plurality of image points of an ultrasound image and to control at least the ultrasound by means of information extracted from the measurement field.

In an ultrasound apparatus in accordance with the invention, for example, an object is imaged by means of ultrasound. An ultrasound transmitter applies sound waves to the object which are reflected to a varying extent by the individual constituents of the object and are detected by an ultrasound sensor. An image of the object can be reconstructed from the different sound reflections in known manner by means of the data processing unit.

An ultrasound apparatus in accordance with the invention has features which are analogous to those of the X-ray system described herein, so that the same or similar advantages are achieved as disclosed in the above description of the X-ray apparatus. Information is again extracted from relevant image regions by means of measurement fields; this information enables control of the sound, for example, the sound dose or sound intensity. Furthermore, control of other system components is also possible. The claims and description are applicable accordingly to the ultrasound apparatus. An ultrasound apparatus of this kind can be used, for example, in the field of medical diagnosis. Automatic adaptation of the system components offers faster and better medical diagnosis, that is, especially in the case of cardiological and gynecological examinations.

The object is also achieved by means of a method as disclosed herein, which method is carried out in an imaging system in order to control the dose of radiation or waves which is applied to an object and necessary for imaging, which method consists of the steps of:

a) forming a measurement field from image points of an image, b) extracting information from the measurement field, and c) controlling the radiation or waves by means of the extracted information.

This method can be used in any imaging system in which automatic control of the radiation or waves or other system components in relation to image regions of interest is particularly advantageous.

The following description, claims and accompanying drawings set forth certain illustrative embodiments applying various principles of the present invention. It is to be appreciated that different embodiments applying principles of the invention may take form in various components, steps and arrangements of components and steps. These described embodiments being indicative of but a few of the various ways in which some or all of the principles of the invention may be employed in a method or apparatus. The drawings are only for the purpose of illustrating an embodiment of an apparatus and method applying principles of the present invention and are not to be construed as limiting the present invention.

DESCRIPTION OF THE DRAWINGS

The foregoing and other features and advantages of the present invention will become apparent to those skilled in the art to which the present invention relates upon consideration of the following detailed description of apparatus applying aspects of the present invention with reference to the accompanying drawings, wherein.

DESCRIPTION

Figure 1:
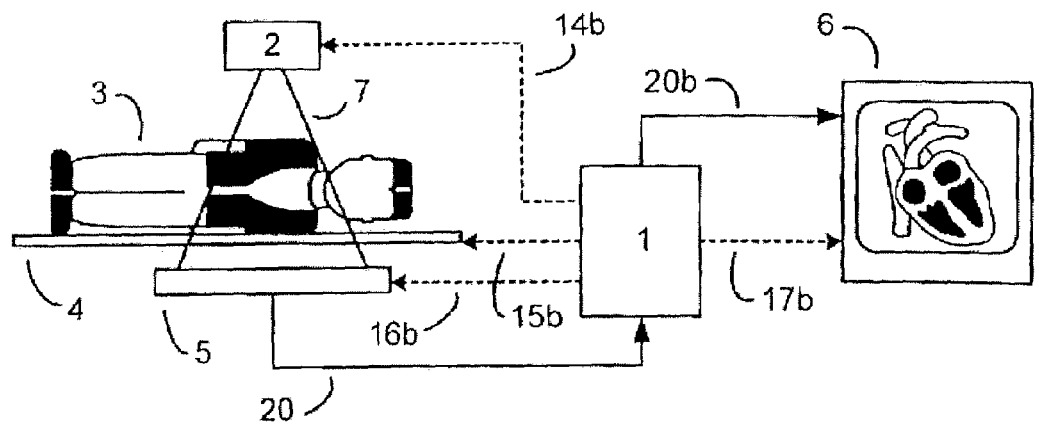
FIG. 1 shows an X-ray examination system which includes aspects for carrying out a method according to principles of the present invention.

FIG. 1 shows the essential components of an X-ray examination system which is suitable for forming a sequence of X-ray images of objects in motion. The system includes an X-ray source 2 which consists of an X-ray tube, the means necessary for the operation of the X-ray tube, for example, a high voltage generator and a power supply unit, and further means for influencing the X-rays such as, for example, mechanical diaphragms. The system also includes an X-ray image detector 5 which outputs digital X-ray images 20; the output rate of the successive images may be so high that an X-ray image sequence in the form of a film can be made presented in real time to the user of the system. The X-ray image detector 5 may consist of a combination of an X-ray image intensifier and a camera or may be formed by a flat digital X-ray detector. The object 3 to be examined, being arranged on a table 4 which can be positioned by means of motors (not shown), is situated between the X-ray source 2 and the X-ray image detector 5. The X-ray source 2, the object 3 and the X-ray image detector 5 are arranged in space in such a manner that the X-rays 7 emanating from the X-ray source 2 can traverse the object 3 so as to be incident on the X-ray image detector 5. The image data produced by the X-ray image detector is applied to an image processing and system control unit 1 which is arranged to prepare the delivered image data for visualization as well as to carry out steps for forming a measurement field and for extracting information; for example, information for the adjustment of system parameters 14b, 15b, 16b, 17b is then extracted from the image data. Such an image processing and system control unit 1 can be formed, for example, by a powerful computer system enabling image processing in real time. The processed image data 20b is applied to a monitor 6 for visualization.

The X-ray source 2, the table 4, the X-ray image detector 5 and the monitor 6 can be adjusted in respect of behavior or working point by means of parameters. In FIG. 1 these parameters are denoted by dashed lines. The parameters 14b of the X-ray source 2 are, for example, the dose of the X-rays, the spectrum of the X-rays and the position or the geometry of the mechanical diaphragms which can be adjusted by way of motors and on the basis of which the shape of the edge region of the radiation cone 7 can be adapted. The parameters 15b of the table are, for example, the position in relation to the radiation cone 7. The parameters 16b of the X-ray image detector are, for example, the sensitivity and the signal amplification. The parameters 17b of the monitor are, for example, the contrast, the brightness and the selection of the most favorable look-up table for grey value adaptation.

In another embodiment the table 4, and hence the object 3 to be examined, is stationary and the X-ray source 2 and/or the X-ray image detector 5 can be displaced and positioned relative to the table 4, for example, by means of appropriate drives, for example, electric motors.

Figure 2:
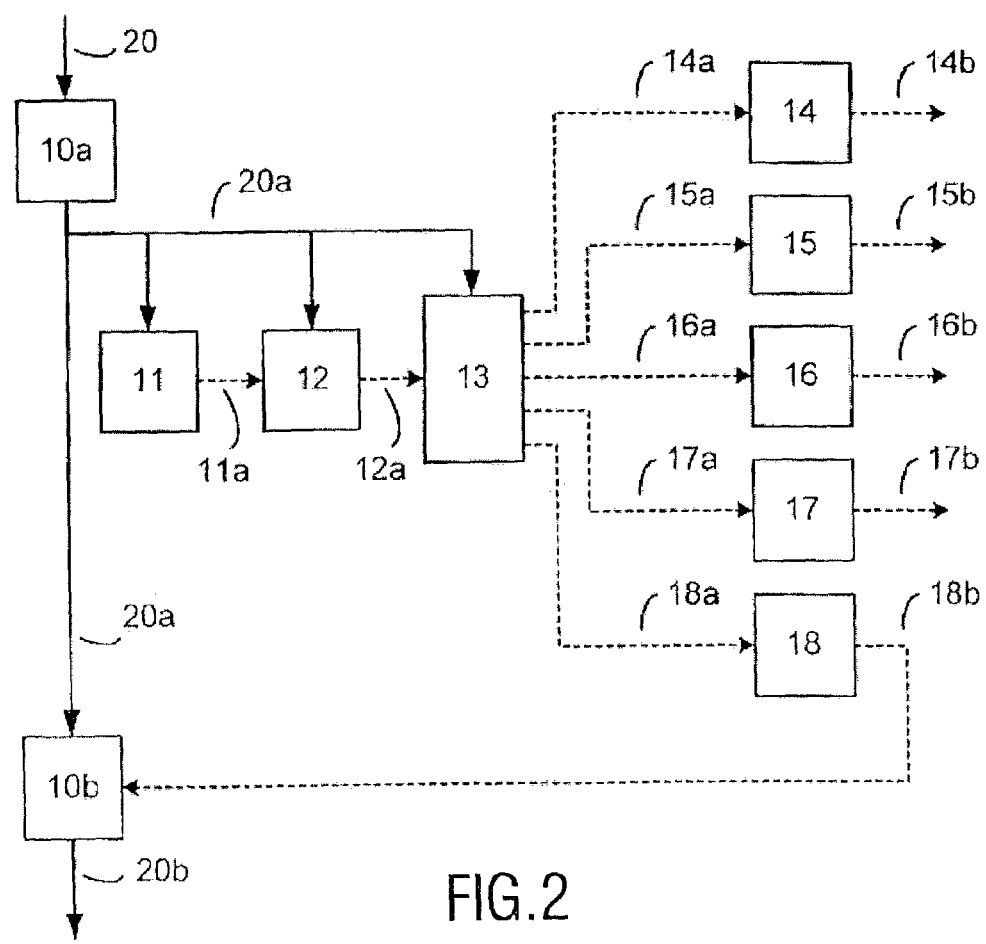
FIG. 2 shows the block diagram of a method according to principles of the present invention.
Figure 3A:
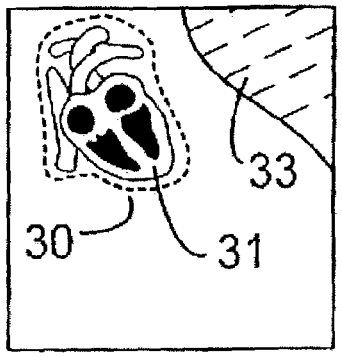
FIG. 3 is a diagrammatic representation of the definition and shifting of a measurement field in an image sequence.
Figure 3B:
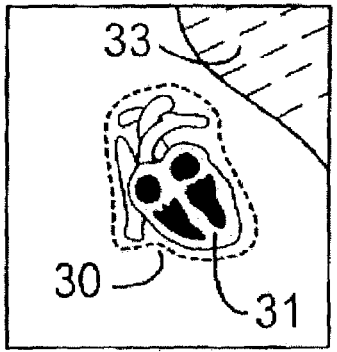
Figure 3C:
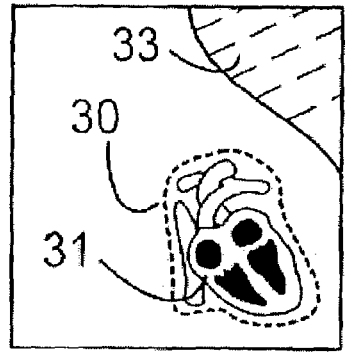
Figure 3D:
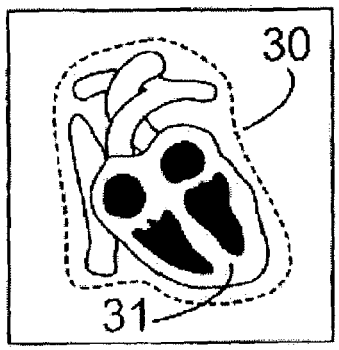
Figure 3E:
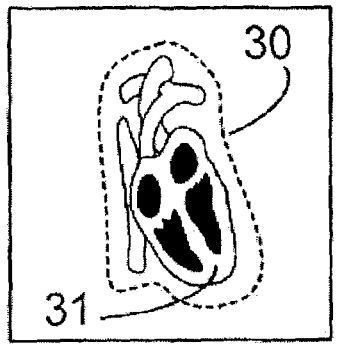
Figure 3F:
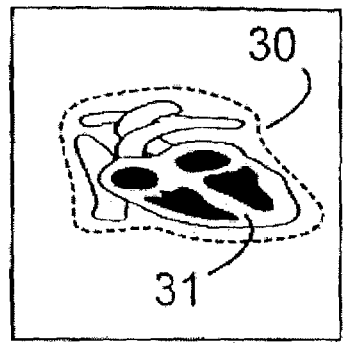
Figure 3G:
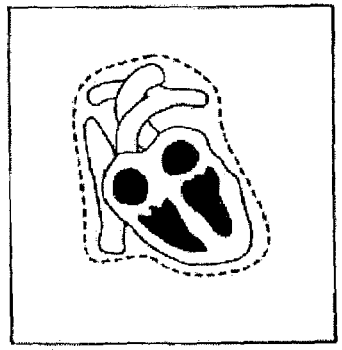
Figure 3H:
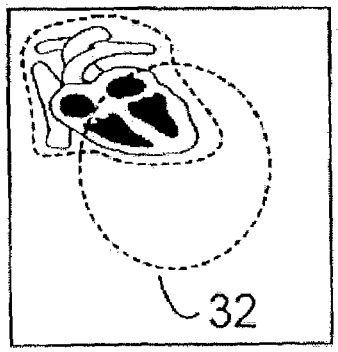
Figure 3I:
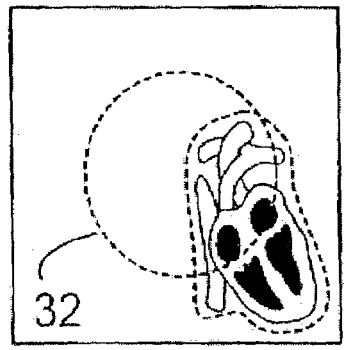

FIG. 2 illustrates schematically, that is, on the basis of a block diagram, the operation of the part of the data processing unit which is used for the formation of the measurement field, the extraction of information and the evaluation of information. All image data is denoted by arrows consisting of a solid line; all other data, such as system parameters or measurement field data, is denoted by arrows consisting of a dashed line.

The incoming image data 20 consists of raw data which is delivered by the X-ray image detector and is full of artifacts; it is applied first to an image pre-processing circuit 10a in order to remove the artifacts. This corrected raw image data 20a is applied to a comparison unit 11 which compares the values of the individual image points with their values from previous images, thus defining which image points are to be attributed to a moving object and which are not to be assigned. This information 11a is applied to a measurement field definition unit 12 which defines one or more measurement fields on the basis of the information 11a and further criteria such as, for example, geometrical proximity relations between the image points. The information 12a concerning the position in space of the measurement fields in the image is applied to an information extraction unit 13 which extracts from the measurement fields the appropriate information 14a, 15a, 16a, 17a and 18a in respect of the parameters occurring in the system.

The information 14a which is extracted from the measurement fields, for example, the brightness or the definition of the image and is used to adjust the parameters of the X-ray generator, is applied to the X-ray generator control circuit 14 which outputs the parameter values 14b, such as the required dose or the geometrical position of the diaphragms, to the X-ray generator 2. The information 15a, for example, the object position in relation to the image edges as required for adjusting the table position, is applied to the table position control circuit 15 which applies the parameter values for table adjustment to the table 4. The information 16a, for example, the dynamic range of the image points which are contained in the corresponding measurement fields and required for adjustment of the X-ray image detector, is applied to the detector control circuit 16 which applies the parameter values 16b to the X-ray detector 5. The information 17a, for example, the contrast and the brightness of the output images as required for adjusting the monitor, is applied to the monitor control circuit 17 which applies the parameter values 17b to the monitor 6.

The image data 20a is applied to a further image processing unit 10b which modifies and optimizes the images in respect of the examination of the object 3 being carried out. This image processing unit may contain algorithms which are adaptive and can be influenced on the basis of algorithm parameters. The information 18a, required for adjusting such algorithm parameters, is applied to the image processing control circuit 18 which applies the parameter values 18b to the image processing unit 10b.

The prepared image data 20b ultimately reaches the monitor 6 on which it is visualized.

FIG. 3 shows three image sequences of three images each so as to illustrate the definition of a measurement field 30. In all images the moving object 31 is formed by a human heart which is capable of moving in itself as well as relative to the image edges. The measurement field 30, whose outer edge or contour is represented by a dashed line, is defined typically in a measurement field definition unit 12 as shown in FIG. 2.

A relative motion of the heart towards the image edges is represented in a first image sequence 3a, 3b and 3c in which the heart moves from the upper left corner of the image to the lower right corner thereof. A second image sequence 3d, 3e and 3f represents a motion of the heart itself. A third image sequence 3g, 3h and 3i shows a motion of the heart which is a combination of the motions of the first two image sequences. All images clearly show that the measurement field always covers the moving heart. It is thus ensured that information concerning, for example, the grey value distribution and brightness, is extracted exclusively from the image region in which the heart is situated so that the system parameters such as image contrast and X-ray dose are optimized on the basis of this information.

However, if the information were extracted from the entire image region, an image region 33 which is shown by way of example in the first image sequence and has been overexposed or underexposed to a high degree would impede optimum adjustment of the system parameters. A static, for example, circular measurement field 32 positioned at the center of the image, as depicted in the third image sequence, would not cover the heart at all times and in the images 3h and 3i it would not produce information that is good enough for optimum adjustment of to system parameters.

Hereinafter, further advantageous examples concerning the defining of the measurement fields and the adjustment of system parameters will be given by way of example.

If the image definition is not good enough in the regions covered by measurement fields, the cause may be an excessively large focal spot in the X-ray tube. If the X-ray tube includes means for adjusting the focal spot, such means can be adjusted on the basis of the system parameters 14b in order to optimize the focal spot.

If there is a risk that the object 31 to be examined moves too close to an image edge, for example, due to a motion of the patient, a system parameter 15 can be used to displace the table 4 so as to move the center of motion of the heart to approximately the center of the image again.

If an image region 33 is overexposed to such an extent that it interferes with the viewing of the X-ray images by the physician or that it has a negative effect on the X-ray image detector in that the image region which directly adjoins the overexposed region is falsified, a measurement field which covers the overexposed region 33 can be defined so that system parameters 14b can be modified in a sense such that the mechanical diaphragms provided in the X-ray source 2 are displaced in such a manner that the region 33 is masked as completely as possible.

The X-ray image detector 5 can be adjusted on the basis of the system parameters 16a. For example, when the system parameters 14b and 15b have already been optimized, the working point of the X-ray image detector can be optimized, so that the entire dynamic range of the detector can be fully utilized in its current mode of operation. When the X-ray image detector is provided with a combination of an X-ray image intensifier and a camera, manifold system parameters, such as the electron beam deflection and focusing of the X-ray image intensifier or the working point of the camera, can be used for optimization.

An image processing unit 10b, comprising adaptive components, is typically used so as to highlight objects or structures represented in the images which are otherwise accessible only with difficulty or not accessible at all. For example, in the case of very noisy images, usually occurring in sequences of X-ray images formed while using a low X-ray dose, the noise can be reduced by means of complex noise reduction algorithms. Such algorithms produce favorable results notably in particular when the behavior of the algorithm is influenced only by the image region of interest to the user. Therefore, the method in accordance with the invention can be advantageously used for optimizing the behavior of the algorithms by the automatic definition and shifting of measurement fields which are particularly suitable in respect of the optimization of the system parameters of the adaptive components.

The adjustments of a means for visualizing the sequence of X-ray images, for example, a monitor 6, can also be automatically optimized by application of the method in accordance with the invention. When all system components participating in the generating and preparation of the image data 20b have been optimized, the user of the system may still be offered a non-optimum image because of an incorrectly adjusted monitor. For example, when the visualization control circuit 17 detects, on the basis of the extracted information 17a, that, despite the optimization of the other system components, the X-ray image still has a comparatively low contrast at the area of the measurement field, that is, in the image region of particular interest to the user, the monitor 6 can be adjusted, via its system parameters, in such a manner that the low contrast of the image is reproduced with the full dynamic range of the monitor. To this end, for example, the contrast adjustment, the brightness and/or the grey value transfer function of the monitor are optimized.

Having described a preferred embodiment of the invention, the following is claimed:

1. An X-ray system for generating X-ray images, which system comprises:
   an X-ray source that provides X-ray image data;
   a data processing unit in which said X-ray data is fed; said data processing unit configured to carry out the processing steps of:
      forming at least one measurement field from a plurality of image points in the X-ray image data, wherein the measurement field is positioned surrounding a region of interest;
      detecting motion of the region of interest;
      reforming the at least one measurement field based on the motion detected; and
      controlling the X-ray source based on information extracted from the measurement field; and
   a display unit for visualizing the X-ray image data processed by the data processing unit.

2. The X-ray system of claim 1 wherein the measurement field is reduced by the image points which are surrounded by more than a selectable number of neighboring image points which are not associated with the measurement field.

3. The X-ray system of claim 1 wherein the system is adapted for cardiological examinations.

4. The X-ray system of claim 3 wherein the data processing unit is arranged to cover at least one of the moving heart, the front part of a catheter present in the body and the tip thereof, by means of at least one measurement field.

5. The X-ray system of claim 1, wherein the information extracted from the measurement field includes at least one of image brightness, region of interest position, and dynamic range of image points.

6. The x-ray system of claim 1, wherein controlling the x-ray source includes adjusting at least one of:
   x-ray dose;
   x-ray spectrum;
   an x-ray focal spot of an x-ray source.

7. The x-ray system of claim 1, further including an x-ray detector, the data processing unit controlling at least one of:
   sensitivity of the x-ray detector; and
   x-ray detector signal amplification.

8. An ultrasound system for generating ultrasound images, which system comprises:
   an ultrasound source that provides ultrasound image data;
   a data processing unit in which said ultrasound data is fed; said data processing unit configured to carry out the processing steps of:
      forming at least one measurement field from a plurality of image points in the ultrasound image data, wherein the measurement field is positioned about a region of interest;
      detecting motion of the region of interest;
      reforming the at least, one measurement field based on the motion detected; and
      controlling the ultrasound source based on of information extracted from the measurement field; and
   a display unit for visualizing the ultrasound image data processed by the data processing unit.

9. The ultrasound system of claim 8, wherein the information extracted from the measurement field includes at least one of image brightness, region of interest position, and dynamic range of image points.

10. A method carried out by an imaging system in order to control a dose of at least one of radiation and waves which are applied to an object for imaging, the method comprising:
    generating a series of images using the at least one of the radiation and waves;
    forming a measurement field positioned enclosing a region of interest for each image in the series of images, the measurement field and the region of interest having different spatial locations in some images of the series of images relative to other images in the series of images,
    detecting motion of the region of interest within the series of images;
    deriving the measurement field based on the motion detected,
    extracting information from the measurement field, and
    controlling the dose in accordance with the extracted information,
    wherein the measurement field includes different portions of the images in the series of images as the region of interest moves.

11. The x-ray system of claim 10, wherein the images are generated using radiation and controlling dose includes controlling a dose of the radiation used to generate the images.

* * * * *